United States Patent [19]

Bryan

[11] Patent Number: 5,667,651

[45] Date of Patent: Sep. 16, 1997

[54] APPARATUS AND ASSOCIATED METHOD FOR REDUCING AN UNDESIRED CONSTITUENT OF GAS ASSOCIATED WITH WASTEWATER AND HAVING SENSOR FAULT DETECTION

[76] Inventor: Avron Bryan, 26 Country Club Rd., Cocoa Beach, Fla. 32931

[21] Appl. No.: 501,843

[22] Filed: Jul. 13, 1995

[51] Int. Cl.$^6$ .................................................. C02F 1/46
[52] U.S. Cl. ........................... 204/401; 95/8; 95/187; 210/916; 205/743
[58] Field of Search ........................... 204/401; 210/916; 95/8, 187; 205/743

[56] References Cited

U.S. PATENT DOCUMENTS

| | | | |
|---|---|---|---|
| 2,782,866 | 2/1957 | Etherington et al. | 183/4.1 |
| 4,094,187 | 6/1978 | Navarre, Jr. | 73/1 G |
| 4,106,916 | 8/1978 | Tuckett et al. | 55/21 |
| 4,151,739 | 5/1979 | Breuer et al. | 73/1 G |
| 4,169,779 | 10/1979 | Tatavia et al. | 204/195 P |
| 4,172,880 | 10/1979 | Tzavos | 423/210 |
| 4,229,411 | 10/1980 | Kisters et al. | 422/62 |
| 4,279,142 | 7/1981 | McIntyre | 73/1 G |
| 4,314,344 | 2/1982 | Johns et al. | 364/500 |
| 4,435,192 | 3/1984 | Stewart | 55/19 |
| 4,578,986 | 4/1986 | Navarre | 73/1 G |
| 4,822,456 | 4/1989 | Bryan | 204/1 T |
| 5,154,734 | 10/1992 | Yung | 55/4 |
| 5,202,637 | 4/1993 | Jones | 204/401 |
| 5,246,594 | 9/1993 | Stegemann et al. | 210/743 |
| 5,356,458 | 10/1994 | Javadi et al. | 95/13 |

FOREIGN PATENT DOCUMENTS

| | | |
|---|---|---|
| 59-142825 | 8/1984 | Japan . |
| 60-106518 | 6/1985 | Japan . |
| 474347 | 11/1975 | U.S.S.R. . |

*Primary Examiner*—Arun S. Phasge
*Attorney, Agent, or Firm*—Allen, Dyer, Doppelt, Milbrath & Gilchrist, P.A.

[57] ABSTRACT

A scrubber apparatus and controller include a gas sensor, and processor for controlling treatment of gas responsive to the sensed undesired constituent so as to enhance reduction of the undesired constituent. The processor further determines a sensor fault and may generate an alarm signal responsive to the sensor fault. The gas sensor is preferably an electrochemical cell comprising an electrolyte and a pair of electrodes associated with the electrolyte. A sensor fault may be determined based upon an impedance of the electrolyte and the pair of electrodes. In addition, the electrochemical cell may include a gas permeable membrane and a pair of electrodes on opposing sides of the membrane to permit determination of damage to the membrane based upon an impedance measurement using the pair of electrodes.

32 Claims, 6 Drawing Sheets

5,667,651

APPARATUS AND ASSOCIATED METHOD FOR REDUCING AN UNDESIRED CONSTITUENT OF GAS ASSOCIATED WITH WASTEWATER AND HAVING SENSOR FAULT DETECTION

FIELD OF THE INVENTION

The present invention relates to pollution control, and, more particularly, to an apparatus and method for reducing an undesired constituent in a gas.

BACKGROUND OF THE INVENTION

Many natural and biological/chemical industrial and municipality processes produce undesired constituents in a gas associated with wastewater. For example, hydrogen sulfide ($H_2S$) and other odorous constituents may be produced from certain types of wastewater. For protection of the environment and for public safety, such undesired constituents are desirably neutralized or reduced in concentration to a non-dangerous and, more preferably, to a non-offensive level, before discharge to the environment.

There are several common conventional approaches for reducing such undesired constituents in the gas associated with wastewater. For example, two approaches withdraw the gas to be treated from the region of generation, and transfer the gas to a scrubbing or cleaning apparatus. In one approach, an absorbent material is used to separate and collect the undesired gaseous constituents before release to the atmosphere. Unfortunately, this approach produces problems of disposal and/or renewal of the spent absorbent material.

A second approach reduces the undesired constituents or components of the gas by application of a solution of scrubbing chemicals and water to the gases flowing within a scrubber vessel. More particularly, scrubbing solution may be contained in a sump connected in fluid communication with a lower portion of the scrubber vessel. The scrubbing solution is withdrawn from the sump, sprayed through the interior of the vessel, and is returned to the sump for further recirculation. Diffusing bodies may also be included within the vessel to increase the area available for chemical reaction between the gas being treated and the scrubbing solution. The chemical processes involved are well known and result in reduced and/or neutralized undesired constituents of the gas discharged to the atmosphere. This second approach may be considered a typical preferred treatment approach.

Unfortunately, operation of a conventional scrubber apparatus may present problems of disposal of the spent scrubbing solution, and the cost of the required treatment chemicals. Moreover, a conventional scrubber may experience significant maintenance difficulties due to corrosion caused by the scrubbing solution and associated high humidity.

A conventional scrubber may also typically use a pH and/or conductivity sensor to measure the concentration and/or activity of the treatment chemical in the scrubbing solution. Treatment chemicals may be added to produce a selected pH and/or conductivity level in the scrubber solution. Accordingly, the control is not directly related to the concentration of the undesired gaseous constituents which may vary by a factor of 100 or more during a typical week (from less than 1 PPB to greater than 300 PPM).

Since pH and/or conductivity control cannot by itself adjust for the varying concentration of the undesired constituents in the gas, excessive treatment chemical consumption typically occurs. In other words, conventional control of the amount of treatment chemical delivered to the scrubbing solution is done rather grossly, and the tendency is to overdose the scrubbing solution with treatment chemicals. This excessive chemical consumption may cause fouling of the diffusing bodies, accelerate corrosion of the vessel and associated components, and require considerable make-up water to be added to the scrubbing solution. In addition, the gross control of the chemistry of the scrubbing solution may also result in failure to sufficiently reduce the undesired constituents with the results being release of noxious or toxic gas. Thus, such a conventional approach typically results in increased operational and maintenance costs, as well as increases the likelihood of damage to the environment.

A wet scrubber is also commonly used for other types of pollution control. For example, a wet scrubber for the metal casting industry is disclosed in U.S. Pat. No. 4,172,880 to Tzavos for removing gaseous pollutants by contact with an acid scrubbing solution. The scrubber is controlled responsive to the electrical conductivity of the scrubbing solution. Along these lines, U.S. Pat. No. 4,229,411 to Kisters et al. discloses an apparatus including sensors for measuring the concentration of various pollutants, and a computer for calculating the necessary amount of neutralizing agent which is introduced into the flow of gas being treated.

Another somewhat related approach to reducing undesired constituents in a gas associated with wastewater includes direct injection of treatment chemicals into the wastewater stream. Direct injection of treatment chemicals is disclosed, for example, in U.S. Pat. No. 5,356,458 to Javadi et al. The patent discloses a system for continuously monitoring the $H_2S$ concentration above a wastewater stream, such as a sewage stream, and for controlling the amount and time of injecting the treatment chemical directly into the wastewater stream to control the $H_2S$ which would otherwise escape or evaporate into the atmosphere. In particular, a gas sample pump moves a sample of gas through a sample line and to the $H_2S$ sensor. Alternately, a sample line may be connected to draw water directly from the wastewater, with the entrained gas being released or removed before reaching the sensor. The $H_2S$ sensor may be connected to a reference or calibration gas, and may be periodically purged by operation of various valves under control of a processor. Unfortunately, directly injecting a chemical into the wastewater stream may be impractical in many situations or may not effectively control the generation or release of $H_2S$ from the wastewater.

Another difficulty with control of undesired constituents in the gas associated with wastewater is that conventional gas sensors, such as for $H_2S$, may be readily damaged or contaminated in the presence of high humidity and corrosive gases—particularly where it is desired to place the sensor in a duct carrying the gas. A conventional $H_2S$ sensor, even if it were to initially survive such a harsh environment, may readily fail or lose calibration during its life. See, for example, G. D. Waltrip, E. G. Snyder, "Elimination of Odor at Six Major Wastewater Treatment Plants," Journal WPCF, Volume 57, Number 10, pg. 1031, October 1985.

SUMMARY OF THE INVENTION

It is therefore an object of the present invention to provide an apparatus and related method for reducing an undesired constituent from a gas associated with wastewater, and while reducing unnecessary consumption of a treatment chemical.

It is another object of the present invention to provide an apparatus and related method for reducing an undesired constituent from a gas associated with wastewater in a reliable and cost effective manner, and while reducing the need for maintenance.

It is yet another object of the present invention to provide an apparatus and related method for reducing an undesired constituent from a gas associated with wastewater incorporating reliable and accurate sensing of the undesired constituent, even in a harsh environment.

These and other objects, advantages and features of the present invention are provided by a scrubber apparatus and controller including gas sensor means, and processor means for controlling treatment means responsive to the sensed undesired constituent so as to enhance reduction of the undesired constituent, and wherein the processor means further comprises sensor fault testing means for determining a sensor fault. The processor means preferably further comprises alarm generating means for generating either a local or remote alarm signal responsive to the sensor fault testing means determining a sensor fault. Accordingly, the reliability of the scrubber apparatus is greatly enhanced.

The scrubber apparatus is preferably for treating a gas associated with wastewater to reduce the undesired constituent in the gas. The scrubber apparatus preferably further comprises a vessel, gas flow means for flowing gas to be treated from associated wastewater through the vessel for treatment, and treatment means for reducing the undesired constituent in the gas flowing through the vessel.

The gas sensor means is preferably an electrochemical cell comprising an electrolyte and a pair of electrodes associated with the electrolyte. Moreover, the sensor fault testing means preferably further comprises first impedance measuring means for determining a sensor fault based upon an impedance of the electrolyte and the pair of electrodes. The first impedance testing means may include first impedance comparison means for comparing an impedance measurement of the electrolyte and the pair of electrodes to a predetermined impedance value. The gas sensor means may be periodically calibrated by exposure to a calibrating gas. Accordingly, the first impedance comparison means may also include means for comparing an impedance measurement to a previous impedance measurement associated with a successful prior gas calibration of a sensor.

The first impedance measuring means may comprise a pseudo-noise signal generator operatively connected to the electrolyte and the pair of electrodes. In addition, the first impedance measuring means may comprise correlator means for analyzing the pseudo-noise signal to generate an output signal related to the sensed undesired constituent, and to determine a sensor fault.

Another aspect of the invention relates to determination of a fault of the gas permeable membrane of the electrochemical cell gas sensor. More particularly, the sensor fault testing means may further comprise membrane testing means for determining a sensor fault based on the gas permeable membrane. The membrane testing means may include second impedance measuring means for determining a membrane fault based upon an impedance thereof, as facilitated by a pair of electrodes on opposing sides of the permeable membrane. A measurement of the membrane impedance may be compared to a predetermined value or to a prior known good measured value as determined by a successful calibration of the sensor.

The gas sensor means may be an outlet gas sensor for sensing the undesired constituent in treated gas exiting from an outlet of the vessel. Alternately, or in addition thereto, an inlet gas sensor may be used for sensing the undesired constituent in gas to be treated upstream from an inlet of the vessel. Both sensors may be advantageously monitored according to the invention.

A method aspect of the invention is for reliably controlling a scrubber apparatus for treating a gas associated with wastewater to reduce an undesired constituent in the gas. The scrubber apparatus preferably comprises a vessel, and a sump for containing scrubbing solution. The method preferably comprises the steps of: flowing gas to be treated from associated wastewater through the vessel for treatment; spraying the scrubbing solution in contact with gas being treated for reducing the undesired constituent in the gas, and returning the scrubbing solution to the sump; sensing the undesired constituent by an electrochemical cell gas sensor; controlling a level of treatment chemical in the scrubbing solution responsive to the sensed undesired constituent so as to enhance reduction of the undesired constituent in the gas being treated; and determining a sensor fault of the electrochemical cell gas sensor based upon impedance measuring thereof.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
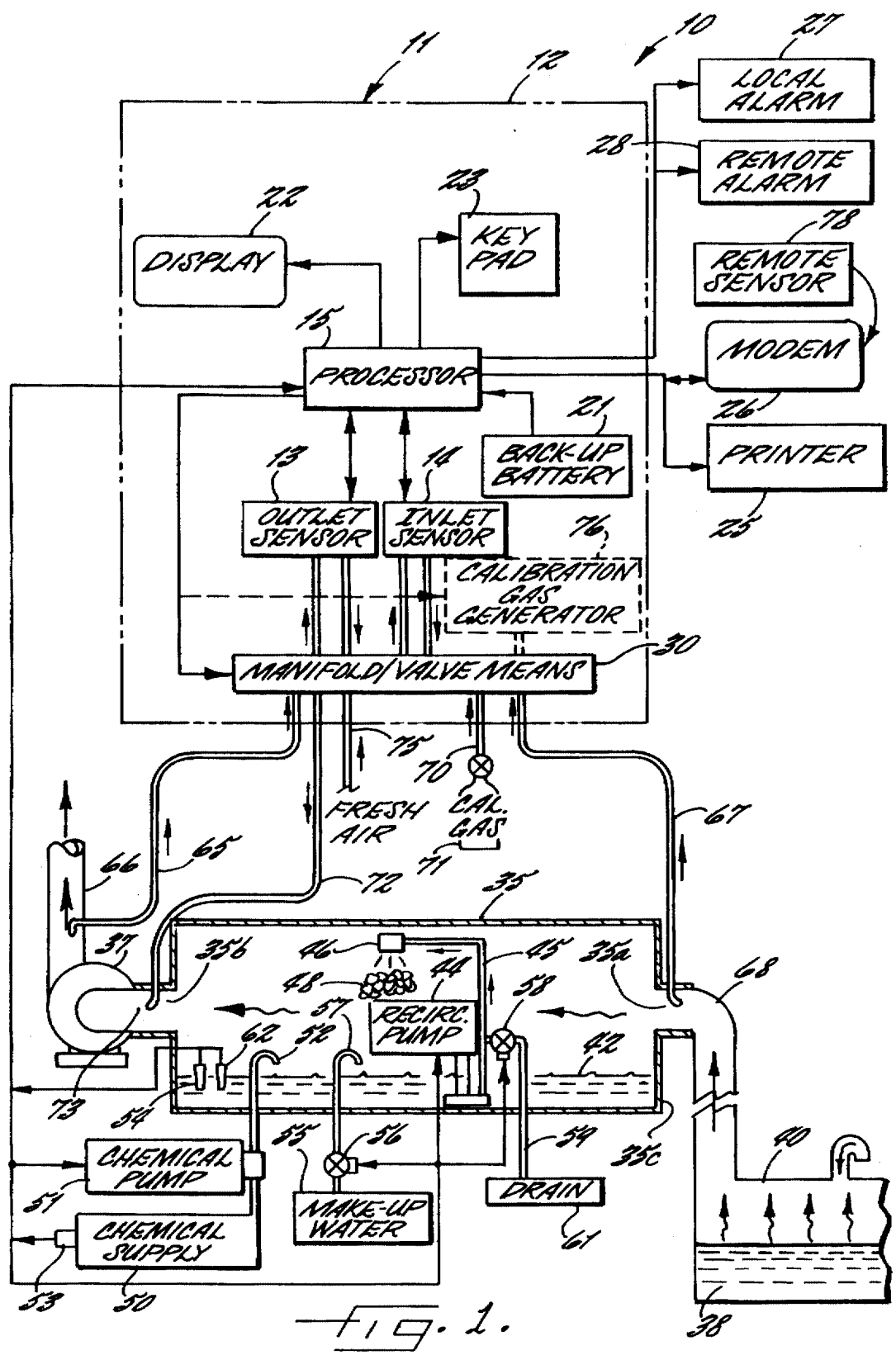
FIG. 1 is a schematic block diagram of the scrubber apparatus and controller in accordance with the present invention.
Figure 2:
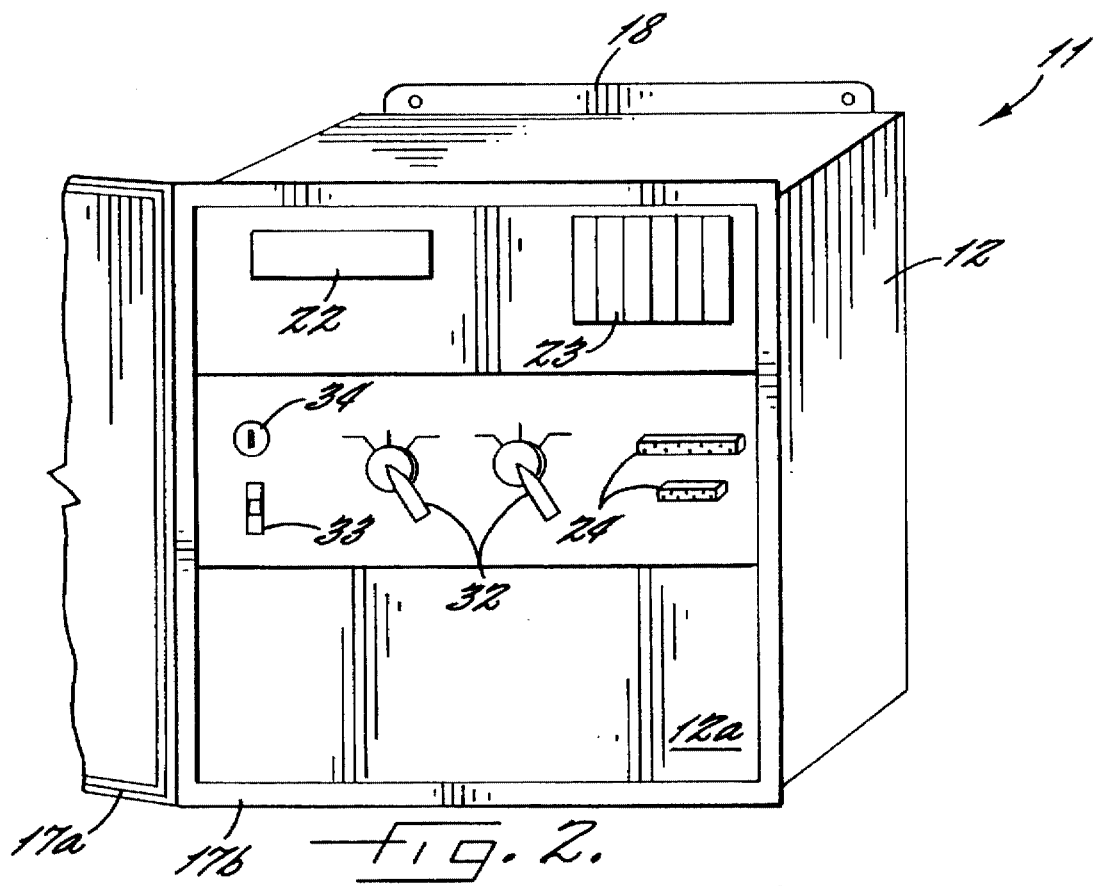
FIG. 2 is a front perspective view of the controller in accordance with the present invention, with the cover door open and partially shown for clarity.

Referring first to FIGS. 1 and 2, the general features and components of a scrubber apparatus 10 and controller 11 in accordance with the present invention are first described. The controller 11 includes an environmentally protective housing 12 illustratively containing an outlet gas sensor 13, an inlet gas sensor 14, and a processor 15 operatively connected to the inlet and outlet gas sensors. Analog signals proportional to the inlet and outlet $H_2S$ concentrations are produced by the inlet and outlet gas sensors, 14, 13 and may be readily interfaced to the processor 15 by analog-to-digital converters (A/Ds), not illustrated.

The housing 12 may preferably be a NEMA 4X rated closure suitable for control panel or wall mounted installation. As shown in FIG. 2, the housing 12 includes a hinged door 16 including a sealing gasket 17a for mating against flange 17b, and the illustrated brackets 18 to facilitate mounting. The housing 12 protects the processor 15 and gas sensors 13, 14 from the external environment, and, more particularly, from high humidity or corrosive gases as may be present around the other portions of the scrubber apparatus 10.

The controller 12 may also include a back-up battery 21, as for retaining memory during a power outage. The controller 11 also illustratively includes a display 22, a keypad 23, and connectors 24 as for interconnecting the processor 15 to a printer 25, or via a modem 26 to a remote computer, not shown. The modem may permit remote access to the information within the processor 15 or permit remote programming of the processor. The display 22 may be driven by the processor 15 to display sensor readings, operating setpoints, or other parameters. The keypad 23 may be used to permit programming of the processor 15, such as to enter certain operating setpoints or other parameters. Moreover, the controller 11 may also be interfaced to a local alarm 27 or a remote alarm 28, as for indicating a sensor failure or other equipment failure, as described in greater detail below.

The controller 11 also includes the illustrated manifold/valve means 30 positioned within the housing 12. The manifold/valve means 30 provides a purge air port, a calibration gas port, a sample gas port, and associated valves for selectively connecting the inlet and outlet gas sensors 13, 14 to desired ports as also described in greater detail below. The manifold/valve means 30 may be selectively operable either under control of the processor 15 or by manual selector switches 32 on the front panel 12a of the housing 12 (FIG. 2). The controller 11 may also include an on/off switch 33 and a key switch 34 mounted on the front panel 12a of the housing 12 (FIG. 2).

Turning now to other portions of the scrubbing apparatus 10, the scrubbing apparatus includes a vessel 35 having an inlet 35a and an outlet 35b. In addition, gas flow means is provided by the illustrated suction blower 37 for flowing gas to be treated from associated wastewater 38 through the vessel inlet 35a, through the vessel 35 for treatment, and exiting from the vessel outlet 35b after treatment. The gas to be treated is being collected from a portion of a wet well 40, although those of skill in the art will readily recognize that other sources of gas associated with wastewater may also be beneficially treated by the scrubbing apparatus 10 in accordance with the invention.

The scrubber vessel 35 also includes a sump 35c defined in a lower portion of the vessel for containing scrubbing solution 42 therein. The scrubbing apparatus 10 also includes recirculating spray means provided by the illustrated recirculation pump 44, piping 45 and spray head 46 for drawing scrubbing solution 42 from the sump 35c, spraying the scrubbing solution in contact with gas being treated within the vessel 35, and for returning scrubbing solution back to the sump. The scrubber apparatus 10 may also include diffusing bodies 48, only several of which are shown for clarity, being positioned within the vessel 35 and through which the gas to be treated flows for increasing contact between sprayed scrubbing solution and the flowing gas.

In addition, the scrubber apparatus 10 includes treatment chemical supply means provided by the illustrated chemical supply 50, chemical pump 51 and associated piping 52 for controllably delivering treatment chemical to the scrubbing solution responsive to the processor 15 of the controller 11, as described in greater detail below. A treatment chemical level sensor 53 is also preferably provided so that the processor 15 may give an alarm indication responsive to a low level of remaining treatment chemical in the chemical supply container 50.

As used herein the terms "treatment chemical" and "treatment chemicals" are used interchangeably, it being understood that either term may cover a solution including a single or multiple chemicals added to water to form the scrubbing solution 42. For example, to reduce $H_2S$, a typical significant undesired constituent associated with wastewater 38, sodium hydroxide may be used in the scrubbing solution 42. Other odorous or noxious constituents may also be removed by the scrubbing apparatus 10 according to the invention with the proper application of treatment chemistry, as would be readily appreciated by those skilled in the art.

The scrubber apparatus 10 also includes a scrubbing solution sensor 54 for sensing a characteristic of the scrubbing solution 42. Accordingly, the processor 15 may further control the level of treatment chemical in the scrubbing solution responsive to the sensed characteristic of the scrubbing solution. The scrubbing solution sensor 54 may sense pH, conductivity, oxidation reduction potential (ORP), dissolved oxygen, or other pertinent quantities as would be readily understood by those skilled in the art.

As illustrated in the lower portion of FIG. 1, means may be provided for adding make-up water including the make-up water source 55, an associated control valve 56 operable by the processor 15, and associated piping 57 for delivering make-up water to the sump 35c. Draining means may also be provided to reduce the liquid level within the sump 35c. The draining means may be provided by the illustrated recirculating pump 44, associated drain valve 58 controllable by the processor 15, associated drain piping 59, and the schematically illustrated drain 61. A liquid level sensor 62 may also be provided to provide the processor 15 with an indication of the liquid level within the sump 35c.

Tubing is used to connect the various ports of the manifold/valve means 30 to respective portions of the scrubber apparatus 10. Outlet sensor tubing 65 connects the outlet sensor port to an outlet duct of the apparatus, inlet sensor tubing 66 connects the inlet sensor port, and calibration tubing 70 connects an external calibration source 71 to the calibration port. In addition, suction line tubing 72 connects the vacuum or suction port to a portion of the outlet duct upstream from the vacuum blower 37, and a short length of purge air tubing 75 is connected to the purge air port of the manifold/valve means 30. The inlet and outlet gas samples from the vessel 35 are extracted, treated for humidity levels, such as using a Peltier effect unit within the housing, and applied to respective gas inlet and outlet sensors, 14, 13, respectively.

In addition to or as an alternative to the external calibration gas source 70, an internal calibration gas generator 76 may be provided for generating a known concentration of $H_2S$ by electrolysis, for example, as would be readily understood by those skilled in the art.

A remote gas sensor 78 may also be connected to the gas to be treated at a point substantially upstream from the vessel inlet 35a. In other words, the modem 26, for example, may be used to connect to a sensor at a remote sensing position. As will be explained herein, the remote sensing may permit greater efficacy of feedforward control of the level of treatment chemical in the scrubbing solution 42.

The processor 15 may further comprise make-up water adding means for controlling addition of make-up water to the scrubbing solution contained within the sump responsive to the scrubbing solution sensor 54. Also relating to the control of the liquid level within the sump, the scrubber apparatus 10 preferably also includes draining means for controllably draining scrubbing solution contained within the sump. Thus, the processor 15 preferably further comprises scrubbing solution calculating means for determining dissolved salts or other contaminants within the scrubbing solution being above a predetermined threshold and cooperating with the draining means for draining a portion of scrubbing solution 42 responsive to the calculated salts being above the predetermined level.

Figure 3A:
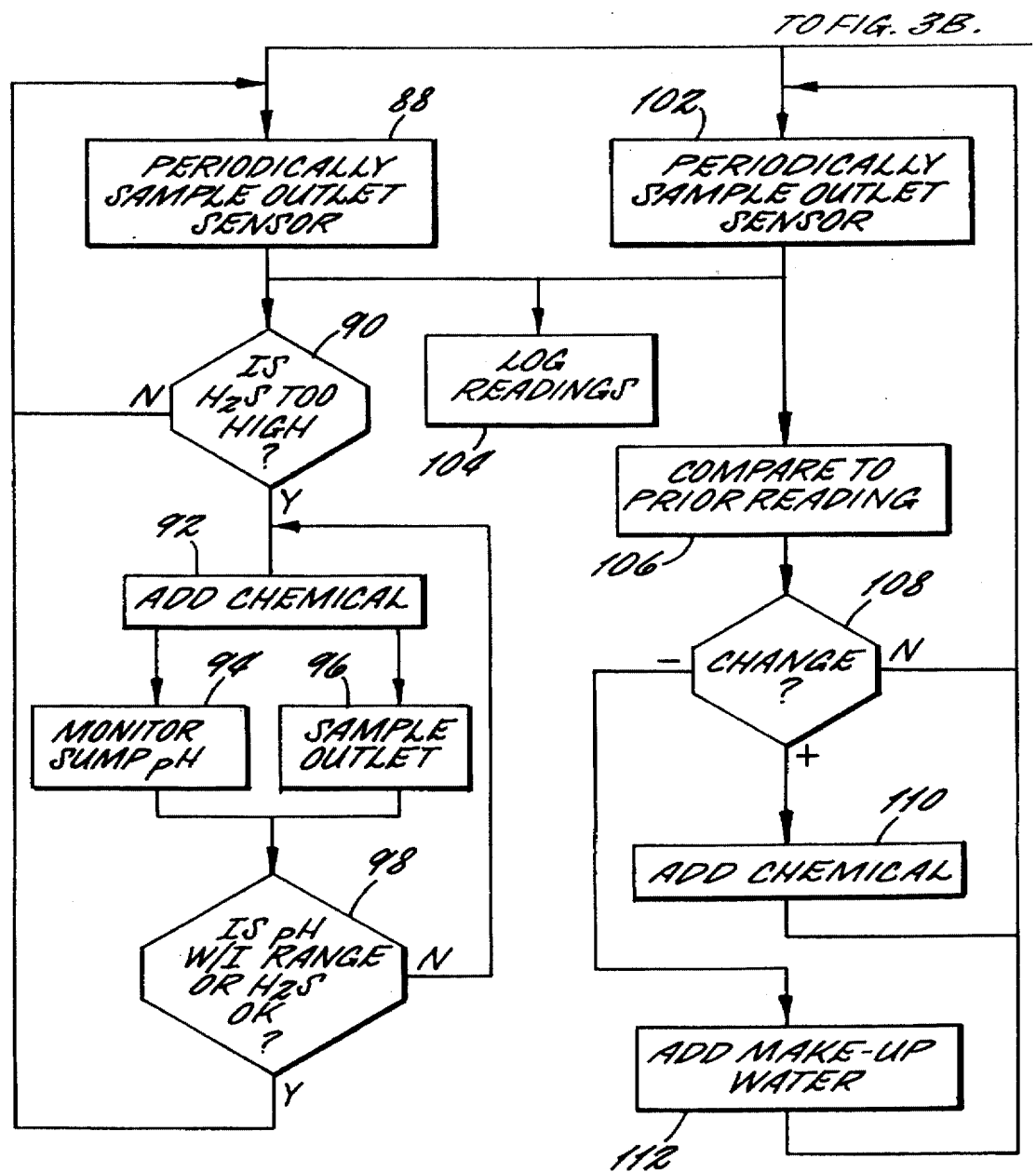
FIG. 3A is a portion of a flow chart illustrating operation of the scrubber apparatus and controller as shown in FIG. 1.
Figure 3B:
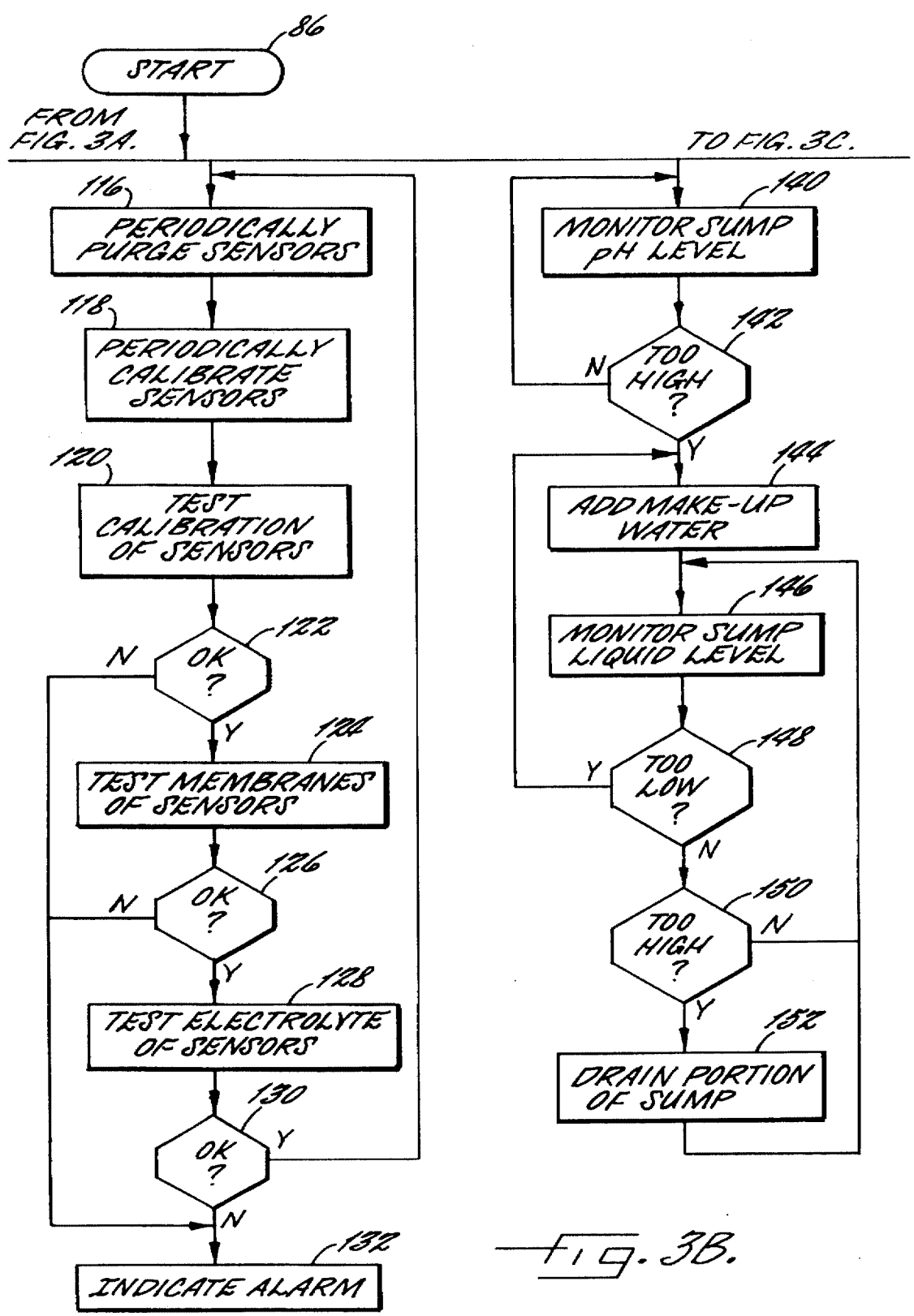
FIG. 3B is a continuation of the flow chart shown in FIG. 3A illustrating operation of the scrubber apparatus and controller as shown in FIG. 1.
Figure 3C:
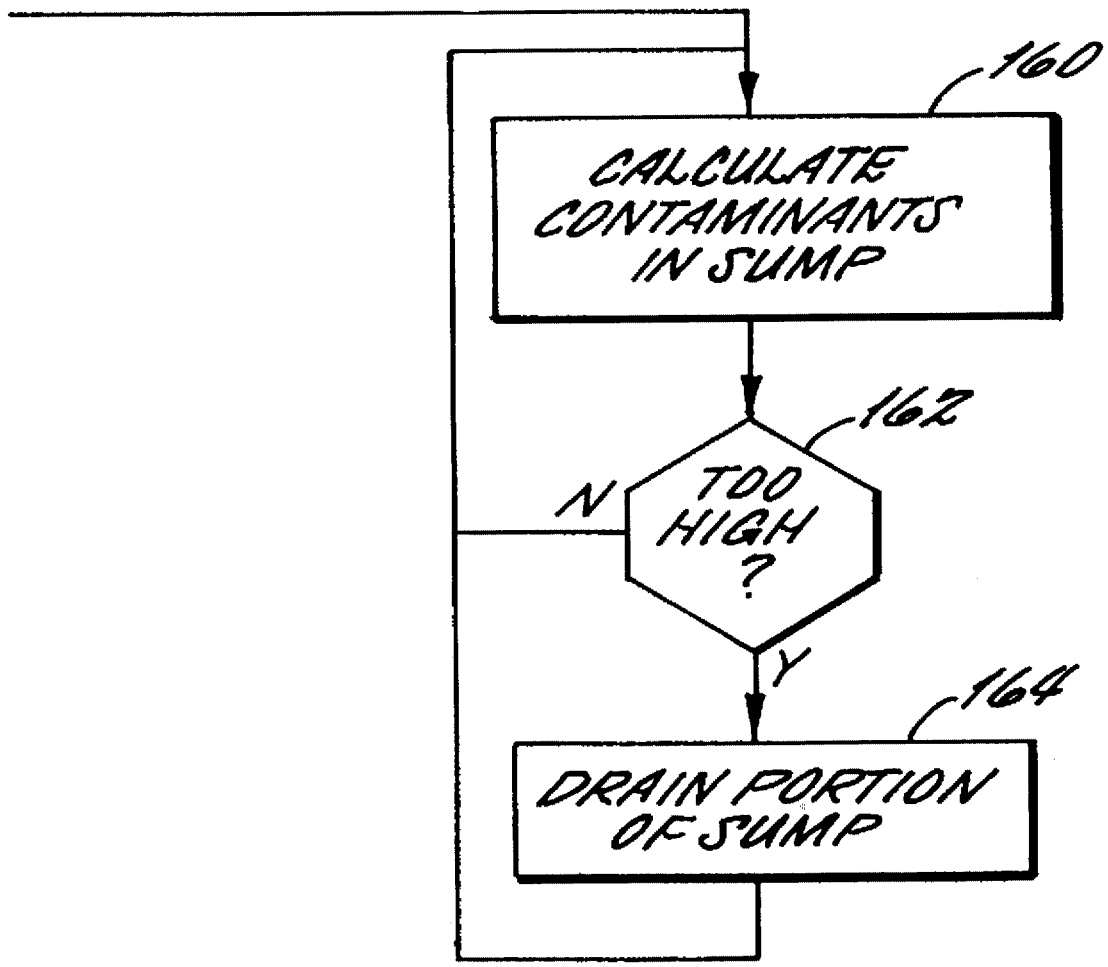
FIG. 3C is a continuation of the flow chart shown in FIGS. 3A and 3B illustrating operation of the scrubber apparatus and controller as shown in FIG. 1.

Turning now additionally to the simplified flow chart of FIGS. 3A, 3B and 3C, further operation and features of the scrubber apparatus 10 and controller 11 in accordance with the present invention are explained. The flow chart is by way of example directed to reduction of $H_2S$, although alternative or additional undesired constituents may also be similarly removed, as would be readily understood by those skilled in the are. From the start (Block 86), the processor 15 causes continuous periodic sampling of the gas outlet sensor 13 at Block 88. The periodic sampling provides an extended life for the sensor 13, while still providing sufficient information for accurate control. For example, for each ten minute period, the outlet sensor 13 may sample the outlet gas for nine minutes, and be purged by fresh air for one minute.

The sampling is achieved by selectively coupling the suction tubing 72 in fluid communication with the outlet sensor 13 to thereby draw gas into the sensor. The processor 15 then determines whether the $H_2S$ concentration is above a predetermined threshold, for example, greater than 2 PPM (Block 90). If the concentration is within limits, the operation returns to Block 88 to await another cycle.

If the concentration of $H_2S$ is above the limit, treatment chemical is added at Block 92. The treatment chemical is added to the scrubbing solution 42 on a proportional basis and is thoroughly mixed by scrubber action and applied to the gas to be treated during the gas transfer time from the vessel inlet 35a to vessel outlet 35b. The processor may then monitor either or both sump pH (Block 94) and the outlet gas sensor at Block 96. If the pH and the $H_2S$ are within desired ranges, the operation returns to Block 88 to await another cycle. If the pH or the $H_2S$ is outside the desired ranges, more treatment chemical may be added at Block 92 and the treatment process repeated.

In other terms, the present invention provides enhanced reduction of hydrogen sulfide in the gas being treated, and while conserving consumption of treatment chemical. For example, the scrubber apparatus 10 in accordance with the invention may use ⅕ to ⅟₁₅ the amount of treatment chemical as may be used in a prior art scrubber using only pH to control addition of treatment chemicals. Further benefits include reduced fouling of the diffusion bodies 48, reduced operating and maintenance costs, and reduced make-up water requirements among others.

Another aspect of the invention is that the gas inlet sensor 14 may also be continuously periodically sampled or monitored at Block 102. The periodic sampling also increases the inlet gas sensor life. For example, for each ten minute period, the inlet sensor 14 may sample the inlet gas for one minute, and be purged by fresh air for nine minutes. An advantage of sensing the inlet gas, is that readings may be logged or recorded at Block 104 to establish regulatory compliance or to establish efficiency of reduction of the $H_2S$. In addition, if the present gas inlet reading is changed over a prior reading (Blocks 106 and 108) treatment chemical may be added (Block 110) if the level of $H_2S$ has increased (+), or make-up water may be added at Block 112 if the $H_2S$ has decreased sufficiently (−). Accordingly, even greater accuracy of delivery of the treatment chemical is provided to the scrubbing solution 42 to ensure adequate reduction of $H_2S$, while also reducing unnecessary treatment chemical consumption.

Moreover, if an upset is indicated as by a sharp increase in $H_2S$ at Block 108, rather than wait for the outlet gas sensor 13 to detect the increase, the feedforward control is used to promptly add treatment chemical at Block 110. In other terms, feedforward control may be used to assist the control routine in maintaining scrubbing solution 42 pH at a desired minimum value, while still maintaining the ability of the scrubber apparatus 10 to respond predictably and rapidly to time delayed upsets.

As would be readily understood by those skilled in the art, the processor 15 may generate or further refine its operating parameters for adding treatment chemical, for example, based upon past readings. In other words, utilizing a history of the gas sensor data and pH levels, the processor 15 may further determine and refine operating parameters for the scrubbing apparatus 10. As would be readily understood by those skilled in the art, neural network technology may be readily adapted to implement the various control processes described herein.

Other aspects of the invention relate to further ensuring reliable, accurate, and longterm performance of the inlet and outlet gas sensors 14, 13. In particular, as shown in Block 116, each sensor may be periodically purged with fresh air to permit outgassing of $H_2S$ as would be readily understood by those skilled in the art. Such purging may more than double the expected lifetime of the sensors. In addition, each sensor may be periodically calibrated at Block 118 and tested by comparison to a known output function versus a known concentration of $H_2S$ at Block 120. If the sensors are not capable of being calibrated, that is, there is contamination or another sensor defect, an alarm may be indicated at Block 132. The calibration of a sensor may be accomplished at predetermined time intervals under the control of the processor 15, or calibration may be initiated by manual control of a selector switch 32 and/or appropriate commands input via the keypad 23.

Figure 4:
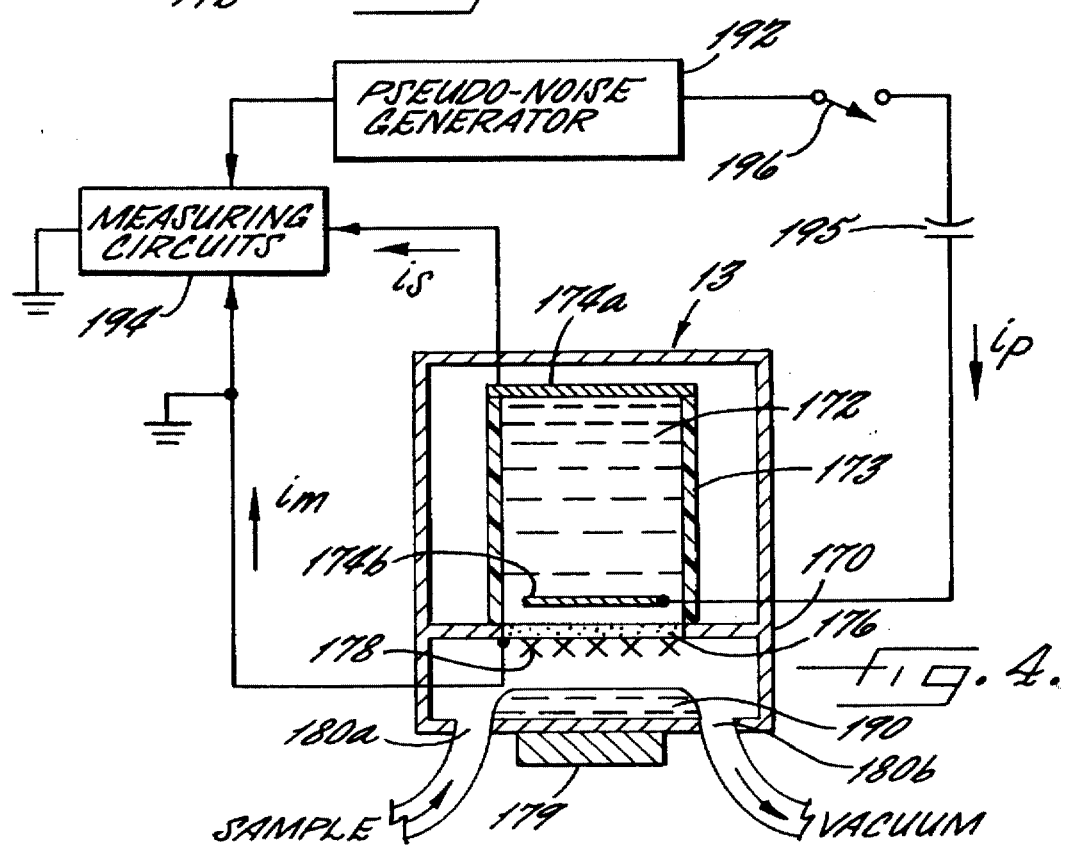
FIG. 4 is a schematic cross-sectional view of a gas sensor and associated circuitry of the scrubber apparatus and controller as shown in FIG. 1.

Referring briefly to FIG. 4, each gas sensor 13, 14 may be an electrochemical $H_2S$ sensor, such as manufactured by City Technology Ltd. of Portsmouth, England under the model designation CITICEL 7HH and modified as described further below. The sensor 13 includes a housing 170, an electrolyte 172 positioned within the interior cylindrical housing 173 and opposing electrodes 174a, 174b thereby defining an electrochemical cell. A gas permeable membrane 176 is positioned adjacent the lower electrode 174b.

A predetermined gas, such as $H_2S$, incident on the outer surface of the membrane 176 diffuses therethrough producing a d.c. potential across the cell electrodes 17a, 174b proportional to the sensed gas concentration. A current in the microamp range may be measured by the external measuring circuit 194. The measuring function may preferably be provided by an A/D converter in cooperation with the processor 15. A grid electrode 178 is positioned adjacent the exterior surface of the permeable membrane. The electrodes 174a, 174b and 176 may be used to determine the integrity of the electrolyte 172 and the integrity of the gas permeable membrane 176 as described in greater detail below.

Returning again to FIGS. 3A, 3B and 3C, the membranes of each sensor may be tested at Block 124 and if a membrane is damaged (Block 126), an alarm may be indicated at Block 132. Similarly, the electrolyte may be tested in each sensor at Blocks 128, 130, and if damaged, or out of the desired range an alarm is indicated at Block 132.

The processor 15 may also monitor sump pH level at Block 140 and if it is too high (Block 142) make-up water may be added (Block 144). Similarly, at Block 146 the liquid level in the sump 35c may be monitored by level sensor 62 (FIG. 1), and if too low (Block 148) water may be added (Block 144). Conversely, if the liquid level is too high, a portion may be drained at Block 152.

Controlled dumping of the scrubbing solution 42 is also typically required to reduce sulfide salt or crystalline concentrations. As illustrated, the processor 15 calculates the salt or other contaminants in the scrubbing solution 42 at Block 160, and if found too high (Block 162), a portion of the scrubbing solution, such as ½ for example, may be drained from the sump 35c (Block 164).

Figure 5:
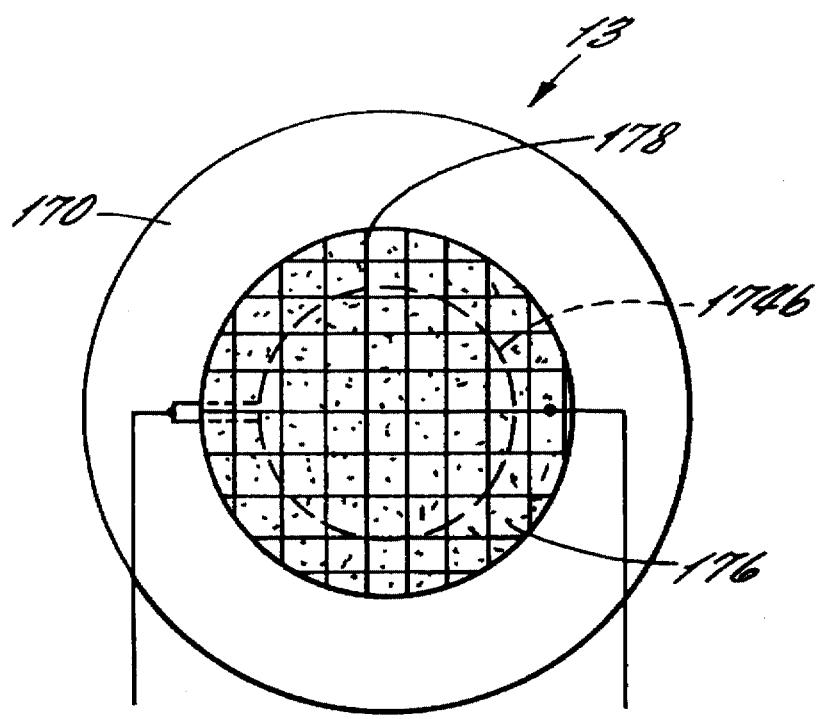
FIG. 5 is a schematic bottom view of the gas sensor shown in FIG. 4 with the sample chamber absent for clarity.
Figure 6:
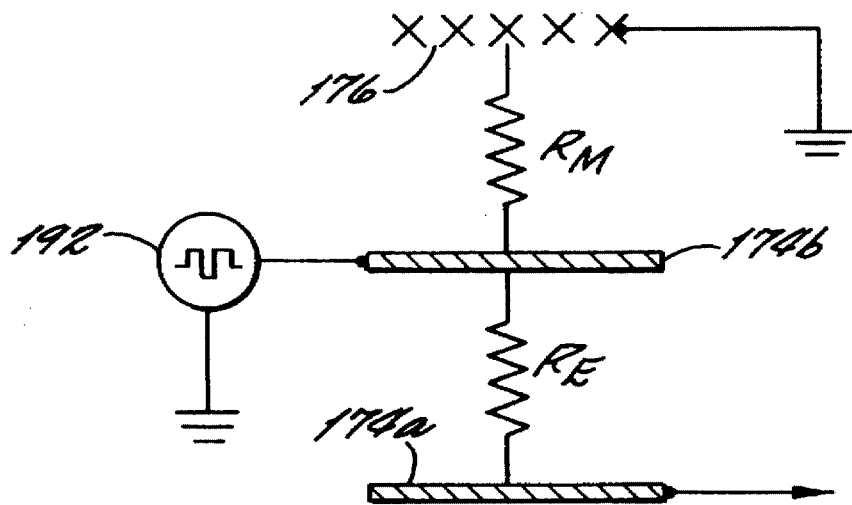
FIG. 6 is a schematic diagram of an equivalent circuit of the gas sensor monitoring circuit as shown in FIG. 4.

Returning now again to FIG. 4, and referring additionally to FIGS. 5 and 6, the gas sensor according to the invention and features and advantages of the sensor are further described. The gas sensor 13 may be an electrochemical sensor including chamber defining means provided by the lower extending portion of the housing 170 cooperating with the permeable membrane 176 for defining a sample chamber therewith and having a gas entry port 180a and a gas exit port 180b opposite the permeable membrane and in spaced relation therefrom. The controller 11 also preferably comprises vertical mounting means for mounting the gas sensor 13 in a vertical orientation within the protective housing 12. For example, the vertical mounting means may be a bracket 179 mounting the gas sensor 13 to the interior side of the front panel 12a. Thus, the gas entry and exit ports 180a, 180b are oriented in a lower portion of the sample chamber to facilitate removal of accumulated liquid 190 within the gas sampling chamber while avoiding contact of accumulated liquid with the permeable membrane 176. Accordingly, the life of the sensor 13 is further extended and reliability thereby increased.

The continued reliable operation of the controller 11 and scrubber apparatus 10 depends upon the integrity of the gas inlet and outlet sensors 14, 13. Thus, the controller 11 provides for monitoring of the operational status of the sensors between calibration periods. Two independent test signals during such periods are generated by the processor 15 and applied to a sensor via a D/A converter, for example. Preferably, one test signal is a pseudo-noise (P/N) sequence applied by the schematically illustrated pseudo-noise generator 192, although other signals that permit cross-correlation may be used. Problems may occur with the sensor, such as deterioration, contamination and depletion of the electrolyte 172 and/or the electrodes 174a, 174b.

The sensor's response to the P/N signal is sampled by the illustrated measuring circuits 194. A cross-correlation analysis is performed to both extract a signal value proportional to the internal impedance of the sensor 13, and simultaneously generate the output signal relating to the sensed gas concentration. If the sensor impedance varies from pre-calibrated limits, a fault is indicated. This technique is discussed in additional detail in U.S. Pat. No. 4,822,456 issued to the present applicant, and the entire disclosure of the patent is incorporated herein in its entirety by reference.

In other words, normal gas concentration is determined by measurement of the current $i_p$. When the switch 196 closes, a time-varying test current $i_p$ produced by P/N signal generator 192 flows, via a blocking capacitor 195 between the cell electrodes 174a, 174b and to the measuring circuit 194. The measuring circuit 194 performs a cross-correlation of the P/N test signal and the sensed gas concentration signal to obtain a measure of the P/N signal current. Variation from normal is indicative of a change in the cell impedance, and may be alarmed. The above described functions may be readily implemented by the processor 15 and associated A/Ds as would be readily understood by those skilled in the art.

The above monitoring procedure will indicate the status of the electrolyte 172 portion of the gas sensor 13. However, other problems can occur as described hereinbelow. A more serious problem may occur when the gas permeable membrane 176 fails due to tiny holes, cuts, etc. Such a problem may cause partial or total sensor failure and, moreover, may not be detected as the sensor may still produce an acceptable level signal. However, the signal may not be related to the sensed gas concentration.

To be able to monitor the status or integrity of the membrane 176, an external platinum electrode 178 in the illustrated form of an open grid is disposed over the external face of the permeable membrane 176 and is connected to the measuring circuit 194 as illustrated. As may be noted in FIGS. 4 and 5, the grid electrode 178 does not interfere with the passage of gas through to the permeable membrane 176. As shown more particularly in the equivalent circuit of FIG. 6, the effective impedance of the cell portion of the sensor 13 is represented by $R_E$ which is typically a relatively high value. The impedance $R_M$ of the gas permeable membrane 176 between the lower cell electrode 174b and the grid electrode 178 is typically very high compared to the cell impedance $R_E$. If the permeable membrane 176 fails, due to a hole, cut, or the like, then $R_M$ may drop by a factor of 100 or more, causing a significant drop in $i_p$, which will be detected, and an alarm can be indicated.

EXAMPLE

An example is included herein for illustration purposes only and is not intended to be limiting of the present invention. A scrubbing apparatus 10 as described above was used to treat gas associated with wastewater in a wet well application. In particular, sodium hydroxide, was used to reduce $H_2S$. The data reproduced in the following TABLE 1 was generated by the inlet and outlet gas sensors 14, 13 indicating variation in the $H_2S$ in the inlet gas stream over approximately 10 minute intervals, along with the corresponding output gas concentration. The readings are in PPM.

TABLE 1

$H_2S$ READINGS

| TIME IN/OUT | TIME IN/OUT | TIME IN/OUT | TIME IN/OUT |
| --- | --- | --- | --- |
| 0:16 59/0 | 0:27 28/0 | 0:38 12/0 | 0:49 2/0 |
| 1:00 1/0 | 1:12 1/0 | 1:23 2/0 | 1:34 0/0 |
| 1:45 1/0 | 1:56 1/0 | 2:00 1/0 | 2:12 1/0 |
| 2:23 1/0 | 2:34 0/0 | 2:45 1/0 | 2:56 1/0 |
| 3:00 1/0 | 3:12 2/0 | 3:23 0/0 | 3:34 1/0 |
| 3:45 1/0 | 3:56 2/0 | 4:00 2/0 | 4:16 1/0 |
| 4:27 0/0 | 4:38 4/0 | 4:49 0/0 | 5:00 4/0 |
| 5:12 1/0 | 5:23 0/0 | 5:34 0/0 | 5:45 12/0 |
| 5:56 2/0 | 6:00 2/0 | 6:12 22/0 | 6:24 2/1 |
| 6:35 25/0 | 6:46 25/0 | 6:57 3/1 | 7:00 3/0 |
| 7:12 20/0 | 7:23 13/0 | 7:34 28/0 | 7:45 18/0 |

TABLE 1-continued

H₂S READINGS

| TIME IN/OUT | TIME IN/OUT | TIME IN/OUT | TIME IN/OUT |
|---|---|---|---|
| 7:56 28/0 | 8:00 28/0 | 8:12 22/0 | 8:23 24/0 |
| 8:34 20/0 | 8:45 15/0 | 8:56 18/0 | 9:00 18/0 |
| 9:12 17/0 | 9:23 20/0 | 9:34 14/0 | 9:45 19/0 |
| 9:56 14/1 | 10:00 14/0 | 10:12 20/0 | 10:23 27/0 |
| 10:35 12/0 | 10:46 5/0 | 10:57 13/0 | 11:00 13/0 |
| 11:12 28/0 | 11:23 12/0 | 11:34 7/0 | 11:45 29/0 |
| 11:56 11/0 | 12:00 11/0 | 12:12 14/0 | 12:23 0/0 |
| 12:34 15/0 | 12:45 15/0 | 12:56 11/0 | 13:00 11/0 |
| 13:12 8/0 | 13:23 11/0 | 13:34 21/0 | 13:45 11/0 |
| 13:56 13/0 | 14:00 13/0 | 14:12 32/1 | 14:23 19/1 |
| 14:34 0/0 | 14:46 9/0 | 14:57 3/0 | 15:00 3/0 |
| 15:12 8/0 | 15:23 12/0 | 15:34 16/0 | 15:45 4/0 |
| 15:56 3/0 | 16:00 3/0 | 16:12 22/1 | 16:23 18/0 |

As can be seen from the data, the scrubber apparatus 10 was effective in reducing the H₂S concentration despite the variability of the inlet gas concentration.

As will now be recognized, a reliable, stand-alone controller, and associated method for optimum control of treatment chemical usage for reducing undesired constituents in a gas associated with wastewater has been disclosed. The control is based on direct measurement of the control variable of interest—the concentration of the undesired constituent of the gas. Other features and advantages are set forth in copending patent application entitled "Apparatus and Associated Method for Reducing an Undesired Constituent of Gas Associated with Wastewater," U.S. Ser. No. 08/501,845, filed Jul. 13, 1995, assigned to the present assignee, and the entire disclosure of which is incorporated herein in its entirety by reference. However, many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed is:

1. A scrubber apparatus for treating a gas associated with wastewater to reduce an undesired constituent in the gas, said scrubber apparatus comprising:
   a vessel;
   gas flow means for flowing gas to be treated from associated wastewater through said vessel for treatment;
   treatment means for reducing the undesired constituent in the gas flowing through said vessel;
   gas sensor means for sensing the undesired constituent; and
   processor means operatively connected to said gas sensor means and said treatment means for controlling said treatment means responsive to the sensed undesired constituent so as to enhance reduction of the undesired constituent in the gas being treated, said processor means further comprising sensor fault testing means for determining a sensor fault of said gas sensor means.

2. A scrubber apparatus according to claim 1 wherein said processor means further comprises alarm generating means for generating an alarm signal responsive to said sensor fault testing means determining a sensor fault.

3. A scrubber apparatus according to claim 1 wherein said gas sensor means comprises an electrolyte and a pair of electrodes associated with said electrolyte; and wherein said sensor fault testing means further comprises first impedance measuring means for determining a sensor fault based upon an impedance of the electrolyte and the pair of electrodes.

4. A scrubber apparatus according to claim 3 wherein said first impedance testing means further comprises first impedance comparison means for comparing an impedance measurement of the electrolyte and the pair of electrodes to a predetermined impedance value.

5. A scrubber apparatus according to claim 4 wherein said processor means further comprises gas calibration means for causing periodical application of a calibration gas to said gas sensor means and calibrating an output thereof based upon the calibrating gas; and wherein said first impedance comparison means comprises means for comparing an impedance measurement to a previous impedance measurement associated with a successful prior gas calibration.

6. A scrubber apparatus according to claim 3 wherein said first impedance measuring means comprises a pseudo-noise signal generator operatively connected to the electrolyte and the pair of electrodes.

7. A scrubber apparatus according to claim 6 wherein said first impedance measuring means comprises first impedance correlator means for analyzing the pseudo-noise signal to generate an output signal related to the sensed undesired constituent, and to determine a sensor fault.

8. A scrubber apparatus according to claim 1 wherein said gas sensor means comprises a gas permeable membrane; and wherein said sensor fault testing means further comprises membrane testing means for determining a sensor fault based on said gas permeable membrane.

9. A scrubber apparatus according to claim 8 wherein said gas sensor means further comprises a pair of electrodes on opposing sides of said gas permeable membrane; and wherein said membrane testing means further comprises second impedance measuring means for determining a membrane fault of the gas permeable membrane based upon an impedance thereof.

10. A scrubber apparatus according to claim 9 wherein said second impedance testing means further comprises second impedance comparison means for comparing an impedance measurement of the gas permeable membrane to a predetermined impedance value.

11. A scrubber apparatus according to claim 10 wherein said processor means further comprises gas calibration means for causing periodical application of a calibration gas to said gas sensor means and calibrating an output thereof based upon the calibrating gas; and wherein said second impedance comparison means comprises means for comparing an impedance measurement to a previous impedance measurement associated with a successful prior gas calibration.

12. A scrubber apparatus according to claim 9 wherein said second impedance measuring means comprises a pseudo-noise signal generator operatively connected to the pair of electrodes on opposite sides of said gas permeable membrane.

13. A scrubber apparatus according to claim 1 wherein said gas sensor means comprises an inlet gas sensor for sensing the undesired constituent in gas to be treated entering an inlet of said vessel.

14. A scrubber apparatus according to claim 1 wherein said gas sensor means comprises an outlet gas sensor for sensing the undesired constituent in treated gas exiting from an outlet of said vessel.

15. A scrubber apparatus according to claim 1 further comprising an environmentally resistant housing containing said processor means and said gas sensor means.

16. A scrubber apparatus according to claim 1 wherein said treatment means comprises:
 a sump, connected in fluid communication with said vessel, for containing scrubbing solution therein;
 recirculating spray means for drawing scrubbing solution from said sump, for spraying the scrubbing solution in contact with gas being treated within said vessel for the undesired constituent in the gas, and for returning the scrubbing solution back to said sump; and
 treatment chemical supply means for controllably delivering treatment chemical to the scrubbing solution.

17. A scrubber apparatus according to claim 16 further comprising scrubbing solution sensor means for sensing a characteristic of the scrubbing solution; and wherein said processor means further controls the level of treatment chemical in the scrubbing solution responsive to the sensed characteristic of the scrubbing solution.

18. A controller for use with a scrubber apparatus comprising a vessel and treatment means for reducing the undesired constituent in the gas flowing through the vessel, said controller comprising:
 a electrochemical cell gas sensor for sensing the undesired constituent in gas associated with the scrubber apparatus; and
 processor means operatively connected to said electrochemical cell gas sensor and the treatment means for controlling the treatment means responsive to the sensed undesired constituent so as to enhance reduction of the undesired constituent in the gas being treated, said processor means further comprising sensor fault testing means for determining a fault of said electrochemical cell gas sensor based upon impedance measuring thereof.

19. A controller according to claim 18 wherein said processor means further comprises alarm generating means for generating an alarm signal responsive to said sensor fault testing means determining a sensor fault.

20. A controller according to claim 18 wherein said electrochemical cell gas sensor comprises an electrolyte and a pair of electrodes associated with said electrolyte; and wherein said sensor fault testing means further comprises first impedance measuring means for determining a sensor fault based upon an impedance of the electrolyte and the pair of electrodes.

21. A controller according to claim 20 wherein said first impedance testing means further comprises first impedance comparison means for comparing an impedance measurement of the electrolyte and the pair of electrodes to a predetermined impedance value.

22. A controller according to claim 21 wherein said processor means further comprises gas calibration means for causing periodical application of a calibration gas to said electrochemical cell gas sensor and calibrating an output thereof based upon the calibrating gas; and wherein said first impedance comparison means comprises means for comparing an impedance measurement to a previous impedance measurement associated with a successful prior gas calibration.

23. A controller according to claim 20 wherein said first impedance measuring means comprises a pseudo-noise signal generator operatively connected to the electrolyte and the pair of electrodes.

24. A controller according to claim 23 wherein said first impedance measuring means comprises correlator means for analyzing the pseudo-noise signal to generate an output signal related to the sensed undesired constituent, and to determine a sensor fault.

25. A controller according to claim 18 wherein said electrochemical cell gas sensor comprises a gas permeable membrane; and wherein said sensor fault testing means further comprises membrane testing means for determining a sensor fault based on said gas permeable membrane.

26. A controller according to claim 25 wherein said electrochemical cell gas sensor further comprises a pair of electrodes on opposing sides of said gas permeable membrane; and wherein said membrane testing means further comprises second impedance measuring means for determining a membrane fault of the gas permeable membrane based upon an impedance thereof.

27. A controller according to claim 26 wherein said second impedance testing means further comprises second impedance comparison means for comparing an impedance measurement of the gas permeable membrane to a predetermined impedance value.

28. A controller according to claim 27 wherein said processor means further comprises gas calibration means for causing periodical application of a calibration gas to said electrochemical cell gas sensor and calibrating an output thereof based upon the calibrating gas; and wherein said second impedance comparison means comprises means for comparing an impedance measurement to a previous impedance measurement associated with a successful prior gas calibration.

29. A controller according to claim 26 wherein said second impedance measuring means comprises a pseudo-noise signal generator operatively connected to the pair of electrodes on opposite sides of said gas permeable membrane.

30. A controller according to claim 18 wherein said electrochemical cell gas sensor is connected in fluid communication with gas to be treated entering an inlet of said vessel.

31. A controller according to claim 18 wherein said electrochemical cell gas sensor is connected in fluid communication with treated gas downstream from an outlet of said vessel.

32. A controller according to claim 18 further comprising an environmentally resistant housing containing said processor means and said electrochemical cell gas sensor.

* * * * *